( 12 ) United States Patent
Yi et al.

(10) Patent No.: US 11,672,435 B2
(45) Date of Patent: Jun. 13, 2023

(54) SENSOR PATCH

(71) Applicant: KOREA INSTITUTE OF SCIENCE AND TECHNOLOGY, Seoul (KR)

(72) Inventors: Hyunjung Yi, Seoul (KR); Tae-Hyung Kang, Seoul (KR); Sunho Kim, Seoul (KR); In-Suk Choi, Seoul (KR); Rhokyun Kwak, Seoul (KR); Sangha Kim, Seoul (KR); Jina Choi, Gwangmyeong-si (KR)

(73) Assignee: Korea Institute of Science and Technology, Seoul (KR)

( * ) Notice: Subject to any disclaimer, the term of this patent is extended or adjusted under 35 U.S.C. 154(b) by 654 days.

(21) Appl. No.: 16/691,006

(22) Filed: Nov. 21, 2019

(65) Prior Publication Data

US 2020/0205673 A1 Jul. 2, 2020

(30) Foreign Application Priority Data

Dec. 31, 2018 (KR) ........................ 10-2018-0173912

(51) Int. Cl.
*G08B 21/04* (2006.01)
*A61B 5/024* (2006.01)
*A61B 5/00* (2006.01)

(52) U.S. Cl.
CPC ............ *A61B 5/024* (2013.01); *A61B 5/6833* (2013.01); *A61B 2560/0412* (2013.01)

(58) Field of Classification Search
USPC ............ 340/539.12, 539.24, 539.22, 539.11, 340/568.1, 691.1, 691.5
See application file for complete search history.

(56) References Cited

U.S. PATENT DOCUMENTS

| 8,116,841 | B2 * | 2/2012 | Bly | ........................ | A61B 5/259 600/382 |
| 8,460,189 | B2 * | 6/2013 | Libbus | ................. | A61B 5/4869 600/386 |
| 8,790,257 | B2 * | 7/2014 | Libbus | ................... | G16H 50/30 600/301 |
| 2009/0093687 | A1 * | 4/2009 | Telfort | ................. | A61B 5/0215 600/300 |
| 2009/0105605 | A1 * | 4/2009 | Abreu | .................. | H04N 5/2256 600/549 |
| 2011/0202005 | A1 * | 8/2011 | Yodfat | .............. | A61M 5/14248 604/151 |
| 2012/0010735 | A1 * | 1/2012 | Gilboa | ................. | H04R 1/1016 381/370 |
| 2012/0256399 | A1 * | 10/2012 | Kokeguchi | ............ | B64D 11/06 280/729 |

(Continued)

FOREIGN PATENT DOCUMENTS

KR 101747416 B1 6/2017
WO 2018004313 A1 1/2018

*Primary Examiner* — Daniel Previl
(74) *Attorney, Agent, or Firm* — Rabin & Berdo, P.C.

(57) ABSTRACT

Provided is a sensor patch configured to be attached to the skin of a user. The sensor patch may include: at least one opening; and a frame surrounding the at least one opening, wherein the frame may include at least one senor configured to measure a biosignal of the user. Therefore, since the at least one sensor for measuring a biosignal is provided on the frame surrounding at least one opening, it may be possible to continuously obtain a biosignal of the user for a long period of time.

9 Claims, 19 Drawing Sheets

(56) References Cited

U.S. PATENT DOCUMENTS

| | | | |
|---|---|---|---|
| 2013/0233063 A1* | 9/2013 | Wang | A61F 13/42 |
| | | | 73/73 |
| 2015/0335288 A1* | 11/2015 | Toth | A61B 5/6833 |
| | | | 600/391 |
| 2018/0271414 A1* | 9/2018 | Deck | H01R 13/625 |
| 2020/0288999 A1* | 9/2020 | Lasarov | A61B 5/0006 |

* cited by examiner (a)

(b)

| Hydrogel | Fractal-cut membrane | HAM |
|---|---|---|
| less-hydrated | Closed | |
| more-hydrated | Open | |

SENSOR PATCH

CROSS-REFERENCE TO RELATED APPLICATION

This application claims the benefit of Korean Patent Application No. 10-2018-0173912, filed on Dec. 31, 2018, in the Korean Intellectual Property Office, the disclosure of which is incorporated herein in its entirety by reference.

BACKGROUND

1. Field

One or more embodiment relates to a sensor patch configured to be attached to the skin of a user.

2. Description of Related Art

In recent years, the role of wearable devices has been emphasized more and more with the advent of the Internet of Things, which enables connection between things and between things and people. Recently, wearable devices for measuring the interaction between the body and external environment agents have been studied.

Customized technology for non-invasive and long-term measurement of biometric information and efficient management of individual's health using the biometric information is emerging as technology that can change the paradigm of the future medical and healthcare industry. Recently, skin mount-type sensors that can be attached to the skin for monitoring biosignals have also been actively researched. Biosignals provide important information for biomedical devices, and multiple biosensors are required to obtain individual signals from multiple points over a wide area.

According to recent studies, sensors using ultra-thin films or adhesive substrates for being mounted on living bodies to obtain biosignals such as electrocardiograms or electromyograms have been developed. In most of the body mount-type sensors of the related art, the sensor platform which covers the skin has a closed structure.

However, since the human skin is an open system in which activities such as moisture evaporation or sweating continuously occur, not only the movement of the human body but also the epidermal loss of moisture, that is, evaporation of moisture through the skin, or the discharge of sweat through the skin has to be considered when it is intended to obtain biosignals by using a sensor for a long period of time.

If a substrate and a sensor are not stretched well when the body moves, or if the adhesion of a substrate is reduced due to moisture discharged from the skin of a user, it may be difficult to continuously obtain biosignals.

In addition, if moisture that has to evaporate from the skin is not properly discharged because of a sensor attached to the skin, users may feel uncomfortable due to the long-time wearing of a sensor, and inconvenience or risks such as itching or necrosis of the skin may also be followed.

In addition, moisture, which is not properly discharged and remains between the skin and a sensor attached to the skin, may markedly lower the adhesion of the sensor to the skin and thus may decrease the accuracy of measurement of biosignals.

Therefore, there is a need for a skin mount-type sensor capable of controlling air permeability and moisture permeability for long-term monitoring of multiple biosignals.

SUMMARY

One or more embodiments include a sensor patch in which at least one sensor is provided on a frame surrounding at least one opening to continuously obtain a biosignal of a user for a long period of time while guaranteeing air permeability and moisture permeability.

Additional aspects will be set forth in part in the description which follows and, in part, will be apparent from the description, or may be learned by practice of the presented embodiments of the disclosure.

According to one or more embodiments, a sensor patch configured to be attached to the skin of a user includes: at least one opening; and a frame surrounding the at least one opening, wherein the frame includes at least one senor configured to measure a biosignal of the user.

In some embodiments, the at least one sensor may include at least one of: a body fluid sensor configured to detect a body fluid of the user; a bioelectrical sensor configured to detect an electrophysiological signal of the user; and a pulse sensor configured to detect a pulse of the user.

In some embodiments, the body fluid sensor may include: at least one body fluid passage configured to discharge the body fluid in a direction away from the skin of the user; and an electrode configured to detect a current flowing through the body fluid of the user which is discharged through the body fluid passage.

In some embodiments, the body fluid passage may have a perimeter unchanging, decreasing or increasing in a direction away from a skin attachment surface of the sensor patch.

In some embodiments, the bioelectrical sensor may include: a hydrogel that has a lower portion making contact with the skin of the user and absorbs moisture from the skin of the user; an electrode configured to detect a current flowing through the hydrogel or biopotential; and an elastic membrane making contact with an upper portion of the hydrogel.

In some embodiments, the elastic membrane may include at least one opening, and as the hydrogel increases in volume, the at least one opening may increase in perimeter such that the moisture absorbed in the hydrogel may be discharged through the at least one opening.

In some embodiments, the frame may include at least one electrode array connected to the at least one sensor.

In some embodiments, the frame may include a unit frame of which both lateral middle portions are bent inward toward the at least one opening.

In some embodiments, the unit frame of the frame may include a plurality of unit frames that are repeatedly arranged such that a pair of vertices of a unit frame may overlap and face a pair of vertices of another unit frame.

In some embodiments, the frame may include: a first unit frame; and a second unit frame, wherein a lower end portion on a side of the first frame may be an upper end portion on another side of the second unit frame.

In some embodiments, when the frame is subjected to tensile stress in a first direction parallel to a surface of the skin to which the sensor patch is attached, the frame may increase in length in the first direction and accordingly in a second direction which is parallel to the surface of the skin and perpendicular to the first direction.

BRIEF DESCRIPTION OF THE DRAWINGS

The above and other aspects, features, and advantages of certain embodiments of the disclosure will be more apparent from the following description taken in conjunction with the accompanying drawings, in which.

DETAILED DESCRIPTION

Figure 1:
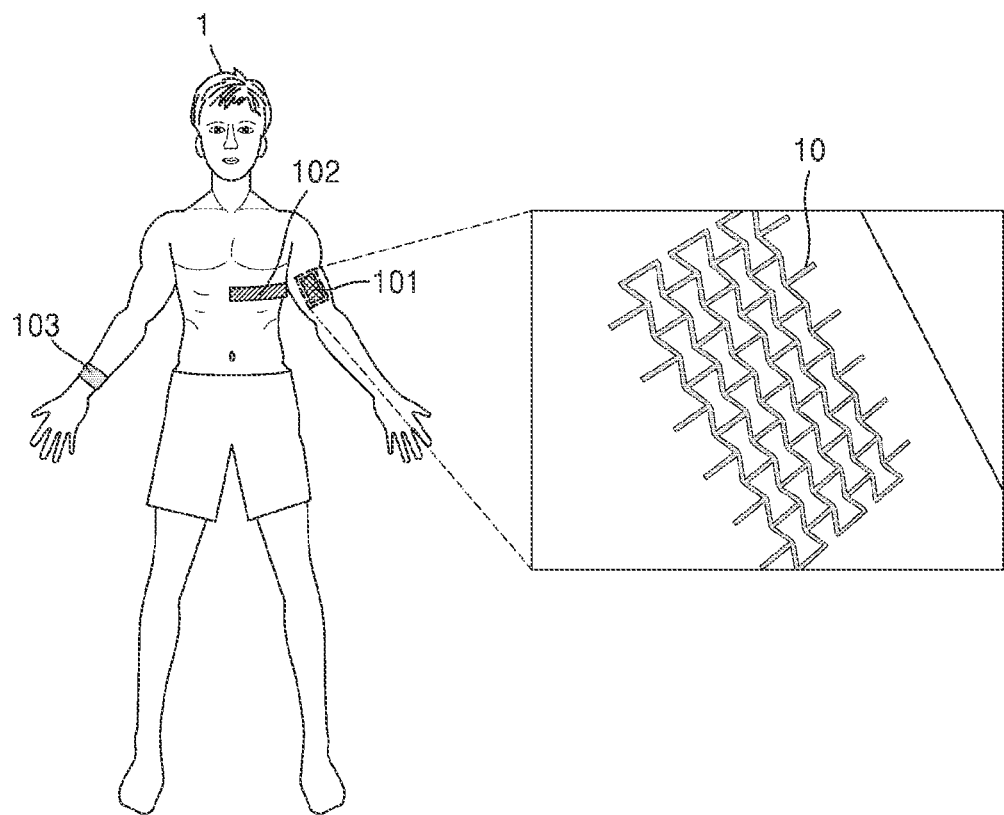
FIG. 1 is a view illustrating an example of a sensor patch according to some embodiments.

Reference will now be made in detail to embodiments, examples of which are illustrated in the accompanying drawings, wherein like reference numerals refer to like elements throughout. In this regard, the present embodiments may have different forms and should not be construed as being limited to the descriptions set forth herein. Accordingly, the embodiments are merely described below, by referring to the figures, to explain aspects of the present description. As used herein, the term "and/or" includes any and all combinations of one or more of the associated listed items. Expressions such as "at least one of," when preceding a list of elements, modify the entire list of elements and do not modify the individual elements of the list.

In the present disclosure, when a portion is referred to as being "connected to" or "coupled to" another portion, the portion may be directly connected to or coupled to the other portion, or may be electrically connected to or coupled to the other portion with another portion therebetween. It will be further understood that the terms "comprises" and/or "comprising" used herein specify the presence of stated features or elements, but do not preclude the presence or addition of one or more other features or elements.

Hereinafter, embodiments of the present disclosure will be described with reference to the accompanying drawings.

FIG. 1 is a view illustrating an example of a sensor patch 10 according to some embodiments.

Referring to FIG. 1, the sensor patch 10 may be attached to the body of a user 1. For example, the sensor patch 10 may be attached to the body of the user 1 using an adhesive layer formed on a lower portion of the sensor patch 10.

The sensor patch 10 may be attached to a surface portion of the body of the user 1 and may be used for at least one of electrocardiogram (ECG) measurement, electromyogram (EMG) measurement, pulse measurement, and body fluid detection.

The sensor patch 10 (101) may be attached to, for example, an arm of the user 1 and may be used to measure an EMG and detect body fluids of the user 1. In another example, the sensor patch 10 (102) may be attached to the chest of the user 1 and may be used to measure an ECG and detect body fluids of the user 1. In another example, the sensor patch 10 (103) may be attached to a wrist of the user 1 and may be used to measure the pulse of the user 1 and detect body fluids of the user 1.

As described above, the sensor patch 10 of the present disclosure may be freely attached to any surface portion of the body of a user according to the measurement or detection target.

Hereinafter, an example structure of the sensor patch 10 will be described according to some embodiments with reference to FIGS. 2A and 2B.

Figure 2A:
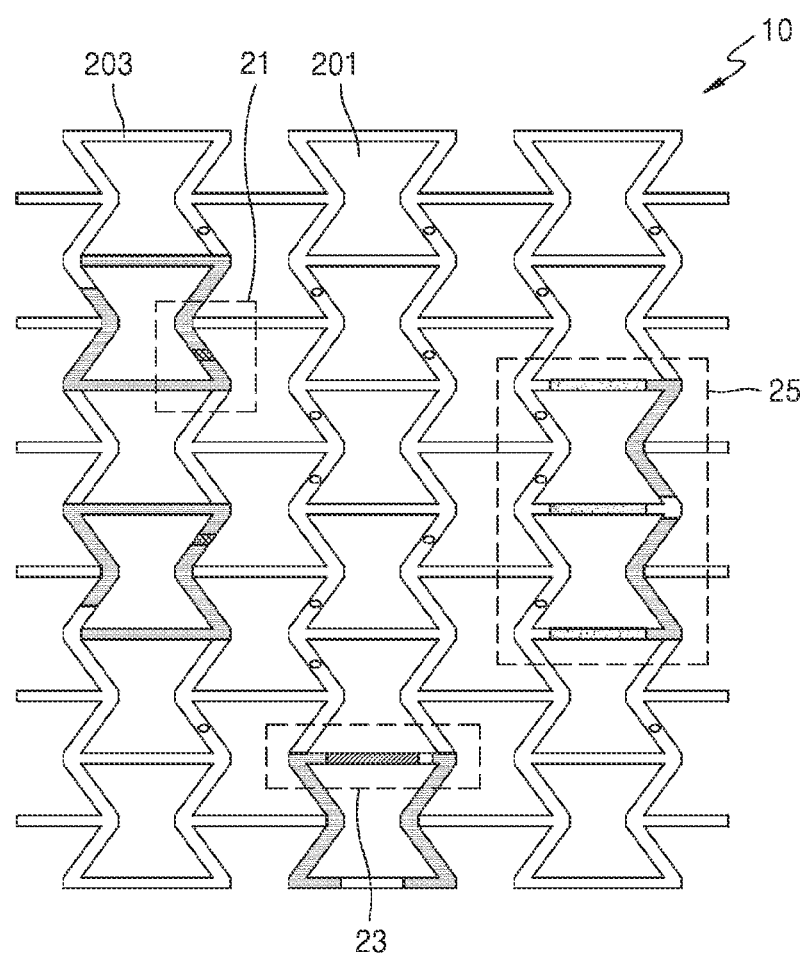
FIGS. 2A and 2B are views illustrating a structure of the sensor patch according to some embodiments.
Figure 2B:
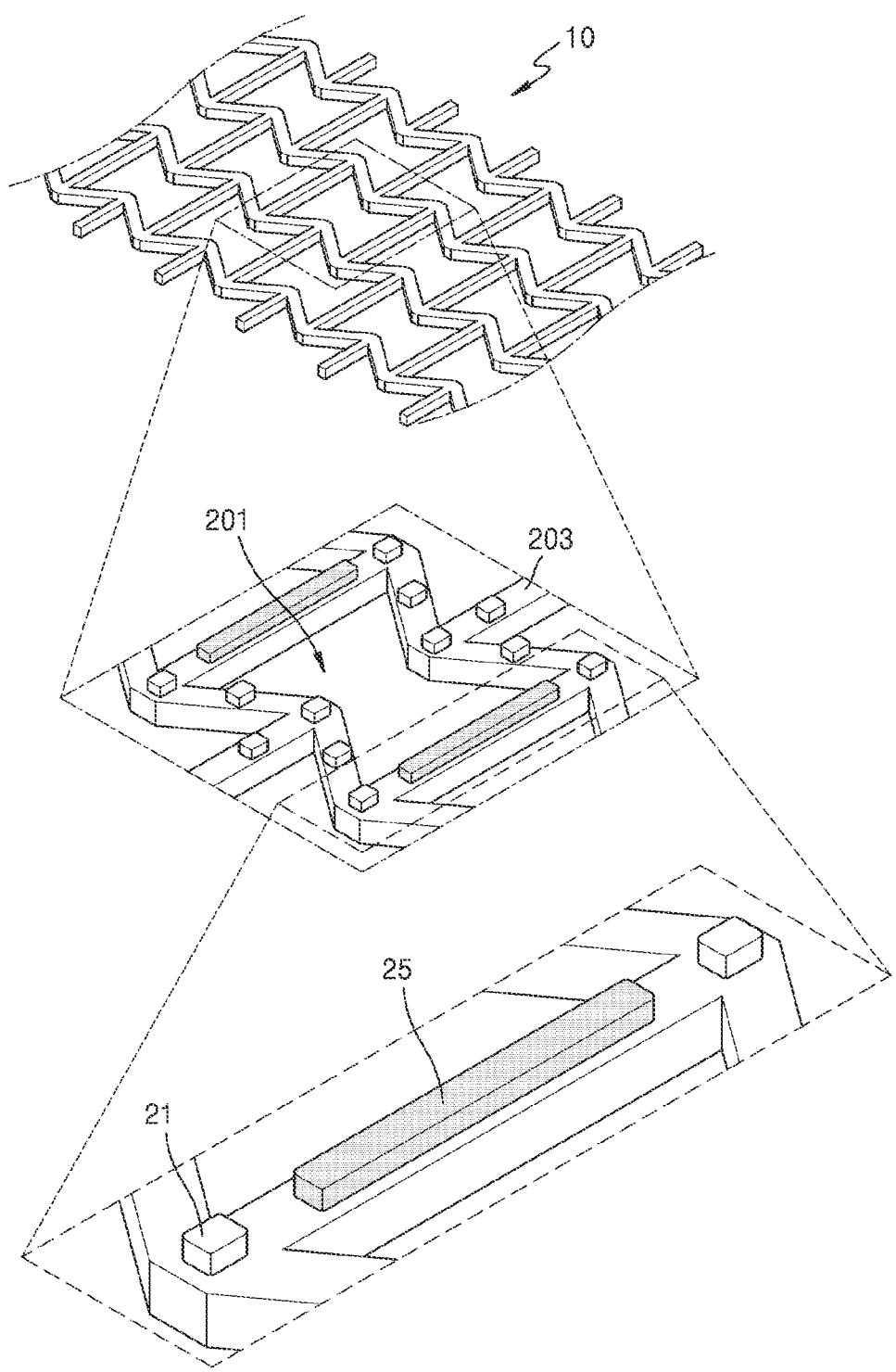

FIGS. 2A and 2B are views illustrating a structure of the sensor patch 10 according to some embodiments.

According to some embodiments, the sensor patch 10 may include at least one opening and a frame surrounding the at least one opening.

Referring to FIG. 2A, in some embodiments, the sensor patch 10 may include openings 201 and a frame 203 surrounding the openings 201.

Moisture, that is, body fluids, contained in the body of the user 1 may be discharged by diffusion or evaporation through the epidermis of the skin of the user 1. In addition, body fluids of the user 1 may be discharged by perspiration through the sweat glands of the skin of the user 1.

When the sensor patch 10 is attached to the skin of the user 1 using the adhesive layer formed on a lower portion of the frame 203, the skin of the user 1 may be exposed through portions other than the frame 203 attached to the skin of the user, that is, through the openings 201.

The sensor patch 10 of the present disclosure partially exposes the skin of the user 1 through the at least one opening 201 when the sensor patch 10 is attached to the skin of the user 1, thereby ensuring a relatively high degree of breathability.

In addition, the sensor patch 10 of the present disclosure is configured to prevent body fluids discharged through the skin of the user 1 from weakening the adhesion of the adhesive layer formed on the lower portion of the frame 203, thereby guaranteeing stable acquisition of biosignals.

In addition, according to some embodiments, the frame 203 surrounding the at least one opening 201 may include at least one sensor for measuring biosignals. Referring to FIG. 2A, in some embodiments, the frame 203 surrounding the openings 201 may include a sensor configured to measure a biosignal.

The sensor may include, for example, a body fluid sensor 21 configured to detect body fluids of the user 1.

The body fluid sensor 21 is a sensor for analyzing body fluids discharged from the skin of the user 1. For example, the body fluid sensor 21 may detect and monitor sweat discharged through sweat glands of the skin of the user 1.

The body fluid sensor 21 may include at least one body fluid passage to allow discharge of body fluids in a direction away from the skin of the user 1. For example, when sweat is discharged from the sweat glands of the skin of the user 1, the body fluid passage of the body fluid sensor 21 may be used as a passage through which the sweat discharged from the sweat glands of the skin of the user 1 moves.

The body fluid sensor 21 may include electrodes configured to detect current flowing through the body fluids of the user 1 that are contained in the body fluid passage.

While sweat discharged from the sweat glands of the skin of the user 1 moves through the body fluid passage, the electrodes of the body fluid sensor 21 may sense current flowing through the sweat. The current flowing through the sweat sensed by the body fluid sensor 21 may be used for generating sensing data.

The body fluid passage may be shaped such that sweat discharged from the sweat glands of the skin of the user 1 may be effectively moved and discharged in a direction away from the skin of the user 1. In addition, the body fluid passage may be shaped such that current flowing through sweat may be effectively detected. For example, the body fluid passage may have a circumference decreasing in a direction away from the skin to which the body fluid passage is attached.

Meanwhile, the at least one sensor may include, for example, a bioelectrical sensor 25 configured to monitor an electrophysiological signal of the user 1.

For example, the bioelectrical sensor 25 may detect bipotential produced in the body of the user 1 to monitor at least one of an ECG and an EMG.

The bioelectrical sensor 25 may include a hydrogel which has a lower portion making contact with the skin of the user 1 and absorbs moisture from the skin of the user 1.

The hydrogel, also called an aquagel, may refer to a substance which has a reticular structure in which a hydrophilic polymer forms three-dimensional crosslinks through physical linking (hydrogen bonds, van der Waals forces, hydrophobic interactions, or polymer crystals) or chemical linking (covalent bonds); does not dissolve in an aqueous environment; but is capable of containing a considerable amount of water owing to internal pores thereof.

The hydrogel of the bioelectrical sensor 25 of the present disclosure is a substance which is capable of transmitting bioelectrical signals of a living body and may be used for a medical device electrode such as an ECG electrode, an electroencephalogram (EEG) electrode, an EMG electrode, a transcutaneous electrical nerve simulator (TENS) electrode, or a high-frequency electrosurgical unit (ESU) ground electrode.

The hydrogel may include various hydrophilic polymers and may thus have various chemical compositions and properties. In addition, the hydrogel may be easily processed and modified in various forms according to applications.

When the hydrogel contains only a certain amount of moisture, the hydrogel may absorb more moisture from the skin of the user 1, and thus the volume of the hydrogel may increase. However, when the hydrogel contains a relatively large amount of moisture, the moisture contained in the hydrogel may evaporate from the surface of the hydrogel, and thus the volume of the hydrogel may decrease.

The bioelectrical sensor 25 may include electrodes to detect a current flowing through the hydrogel or biopotential from the skin of the user 1. While moisture discharged from the skin of the user 1 is absorbed in the hydrogel, the electrodes of the bioelectrical sensor 25 may sense current flowing through the hydrogel from the skin of the user 1. The current sensed by the bioelectrical sensor 25 may be used later for generating sensing data. Also, while moisture discharged from the skin of the user 1 is absorbed in the hydrogel, the electrodes of the bioelectrical sensor 25 may sense biopotential through the skin of the user 1. The biopotential sensed by the bioelectrical sensor 25 may be used later for generating sensing data.

The bioelectrical sensor 25 may include an elastic membrane which is in contact with an upper surface of the hydrogel. The elastic membrane may include at least one opening. As the volume of the hydrogel increases, the circumference of each opening of the membrane may increase to release moisture absorbed in the hydrogel.

In addition, the at least one sensor may include a pulse sensor 23 configured to monitor the pulse of the user 1. The pulse sensor 23 may include, for example, a strain sensor or a pressure sensor that senses a wrist pulse wave of the user 1 at a pulse position.

The strain sensor is a sensor configured to detect mechanical minute variations (strain) by converting the mechanical minute variations into an electrical signal. For example, when the strain sensor is attached to the surface of the skin of the user 1, it is possible to measure minute dimensional variations in the surface of the skin and obtain the pulse of the user 1 from the magnitude and period of the measured variations.

In addition, the pressure sensor is a sensor configured to detect minute variations in pressure by converting the minute variations into an electrical signal. For example, a pressure of several kilopascals (kPa) to several tens of kilopascals (kPa) may be applied to a device by the wrist pulse of the user 1. Thus, minute variations in pressure caused by the pulse of the user 1 may be measured using the pressure sensor attached to the skin, and the pulse of the user 1 may be obtained from the magnitude and period of the measured variations.

The frame 203 may include at least one electrode array connected to the at least one sensor. The electrode array may transmit biosignals obtained from a plurality of sensors.

In the sensor patch 10 of the present disclosure, the at least one sensor and the at least one electrode array may both be formed on the frame 203 surrounding the at least one opening 201, and thus body fluids discharged from the skin of the user 1 may be effectively discharged through the at least one opening 201 regardless of the operation of the at least one sensor.

Referring to FIG. 2B, it is illustrated that the sensor patch 10 including the at least one opening 201 has a three-dimensional structure according to some embodiments. Referring to enlarged portions in FIG. 2B, a plurality of body fluid sensors 21 and a plurality of bioelectrical sensors 25 may be provided on a unit frame of the frame 203.

That is, in the sensor patch 10 of the present disclosure, the position at which at least one sensor is provided on the frame 203 surrounding at least one opening 201 is not limited to any particular position on the frame 203. The position on the frame 203 at which the at least one sensor is provided may be freely determined in the design stage of the sensor patch 10 according to the purpose of use of the sensor patch 10 and the attachment position of the sensor patch 10.

Hereinafter, the structures of the body fluid sensor 21 and the bioelectrical sensor 25 which are examples of sensors that may be included in the frame 203 of the sensor patch 10 will be described according to some embodiments with reference to FIGS. 3A to 7D.

Figure 3A:
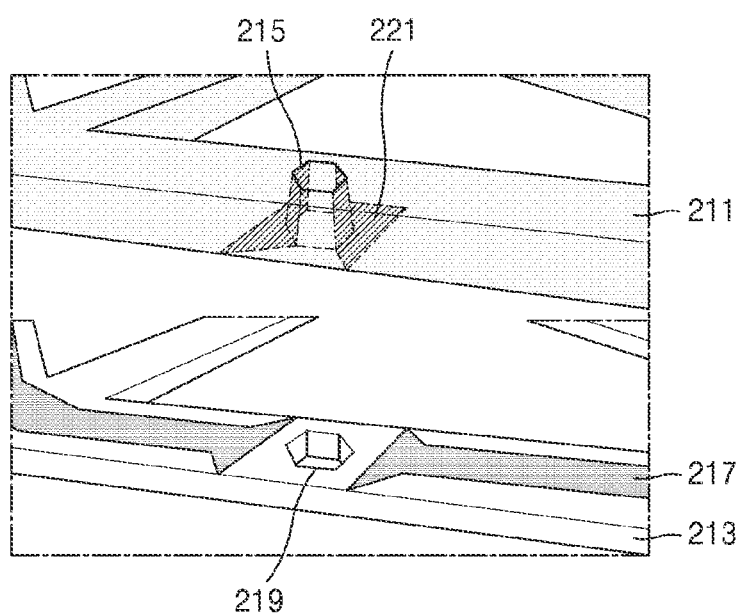
FIGS. 3A and 3B are views illustrating a structure of a body fluid sensor according to some embodiments.
Figure 3B:
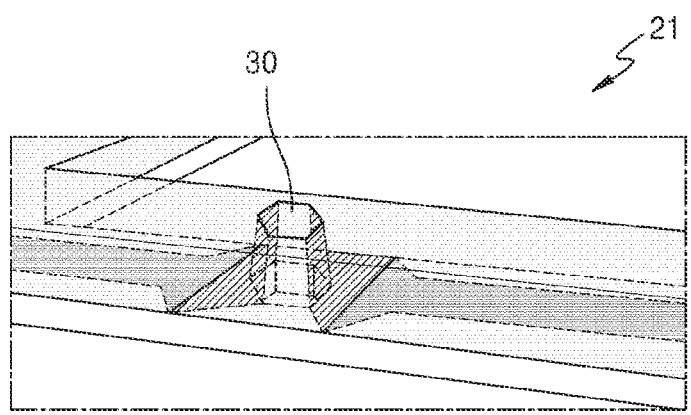

FIGS. 3A and 3B are views illustrating a structure of the body fluid sensor 21 according to some embodiments.

The body fluid sensor 21 according to some embodiments may include: at least one body fluid passage 30 for discharging body fluids in a direction away from the skin of the user 1; and electrodes 221 for sensing current flowing through the body fluids of the user 1 discharged through the body fluid passage 30.

Referring to FIG. 3A, the body fluid sensor 21 may be provided by combining a structural body 211 and a lower plate 213 with each other.

The structural body 211 may include, for example, a first opening 215 forming the body fluid passage 30 for discharging body fluids in a direction away from the skin of the user 1. The electrodes 221 which are capable of detecting current when the body fluid passage 30 is formed may be provided on an inner surface of the first opening 215.

For example, the lower plate 213 may include: a second opening 219 forming the body fluid passage 30 for discharging body fluids in a direction away from the skin of the user 1; and interconnection electrodes 217 connected to the electrodes 221 which detect current flowing in body fluids contained in the body fluid passage 30. Interconnection electrodes 217 may be formed on the bottom side of the structural body 211.

Referring to FIGS. 3A and 3B, the body fluid passage 30 may be formed when the first opening 215 and the second opening 219 are connected to each other by combining the structural body 211 and the lower plate 213 to each other.

When the body fluid sensor 21 included in the sensor patch 10 is brought into contact with the body of the user 1 as the sensor patch 10 is attached to the body of the user 1, the skin of the user 1 may be exposed through the body fluid passage 30 of the body fluid sensor 21.

Body fluids discharged from the exposed skin of the user 1 may be discharged through the body fluid passage 30. For example, when sweat is discharged through the sweat glands of the skin of the user 1, the body fluid passage 30 of the body fluid sensor 21 may function as a passage through which the sweat discharged from the sweat glands of the skin of the user 1 moves.

The body fluid passage 30 may have a structure for effectively moving and discharging body fluids discharged from the skin of the user 1. In addition, the body fluid passage 30 may be shaped such that current flowing through body fluids may be effectively detected. The circumference of the body fluid passage 30 may remain constant or decrease or increase in a direction away from an attachment position on the skin.

FIGS. 4A to 4D are views illustrating a process in which body fluids are discharged through the body fluid sensor 21 according to some embodiments.

Figure 4A:
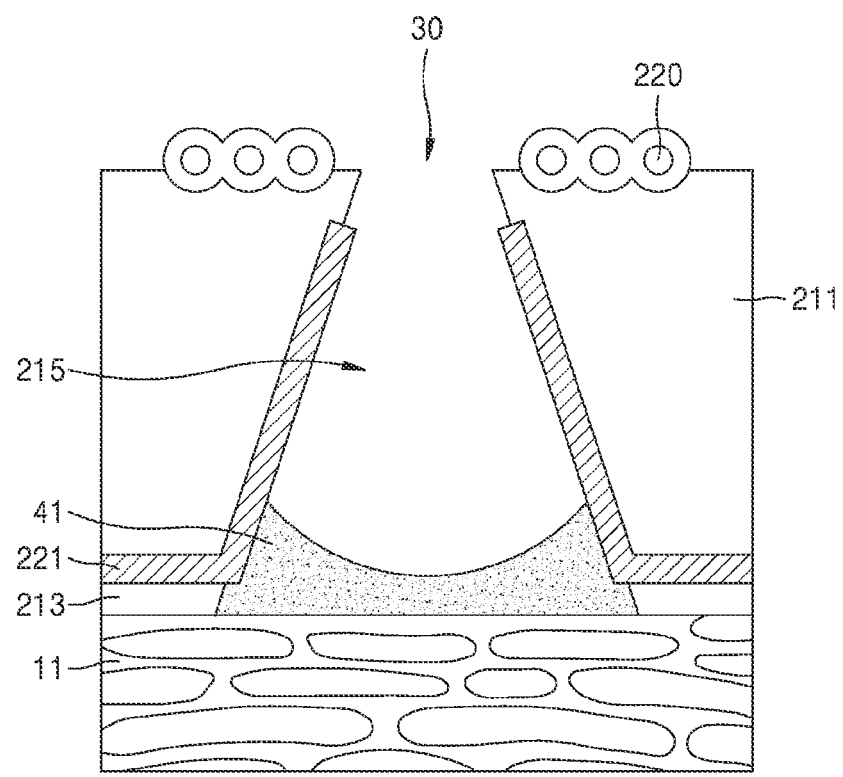
FIGS. 4A to 4D are views illustrating a process of discharging body fluids through the body fluid sensor according to some embodiments.

Referring to FIG. 4A, in some embodiments, the lower plate 213 of the body fluid sensor 21 may be attached to the skin 11 of the user 1.

The electrodes 221 for sensing current flowing in body fluids of the user 1 may be provided on a lateral surface of the first opening 215 of the structural body 211 which has a perimeter decreasing in a direction away from a skin attachment surface of the sensor patch 10, and the electrodes 221 may be connected to the interconnection electrodes 217 for detecting current flowing in body fluids of the user 1.

The body fluid passage 30 for exposing the skin 11 of the user 1 therethrough may be formed by combining the structural body 211 and the lower plate 213 together.

Figure 4B:
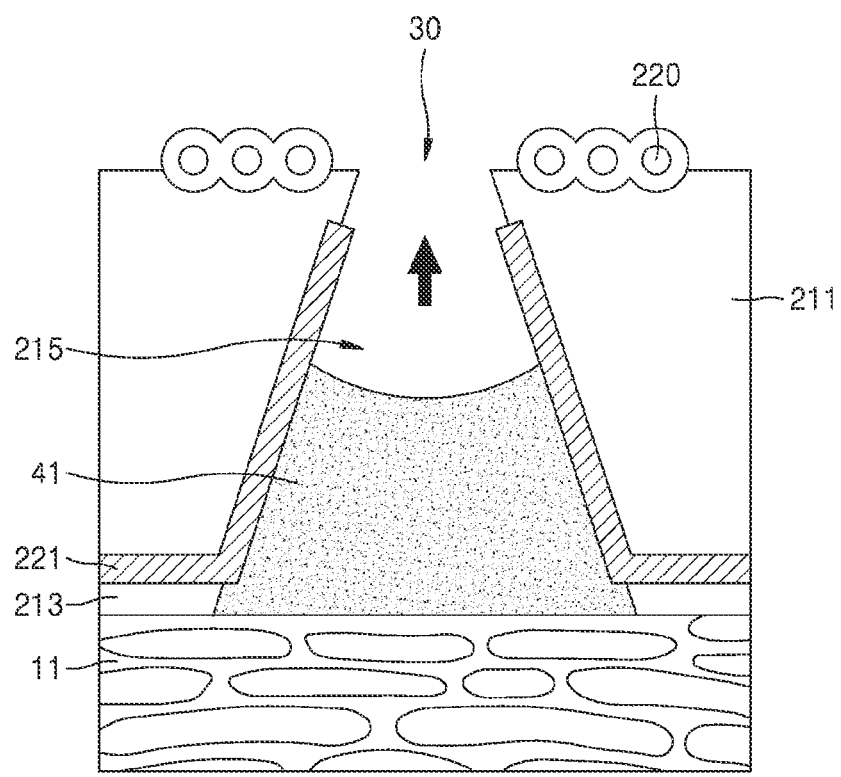

Referring to FIG. 4B, body fluids 41 discharged from the skin 11 of the user 1 may be collected in the body fluid passage 30 by the natural ventilation pressure of the body fluid passage 30. The height of the body fluids 41 collected in the body fluid passage 30 may increase with time.

The body fluids 41 collected in the body fluid passage 30 may connect both the electrodes 221 of the body fluid sensor 21 to allow current to flow between the electrodes 221. The body fluid sensor 21 may generate sensing data about the body fluids 41 based on the current flowing between the electrodes 221 through the body fluids 41. For example, the body fluid sensor 21 may determine the amount of body fluids discharged per unit time from the skin 11 of the user 1 based on the height increase rate of the body fluids 41 in the body fluid passage 30. The electrodes 221 of the body fluid sensor 21 may have a nanonetwork structure, and the nanonetwork structure may have high capacitance, such that variations in current may increase in proportion to variations in body fluids, and the body fluid sensor 21 may have high sensitivity.

Figure 4C:
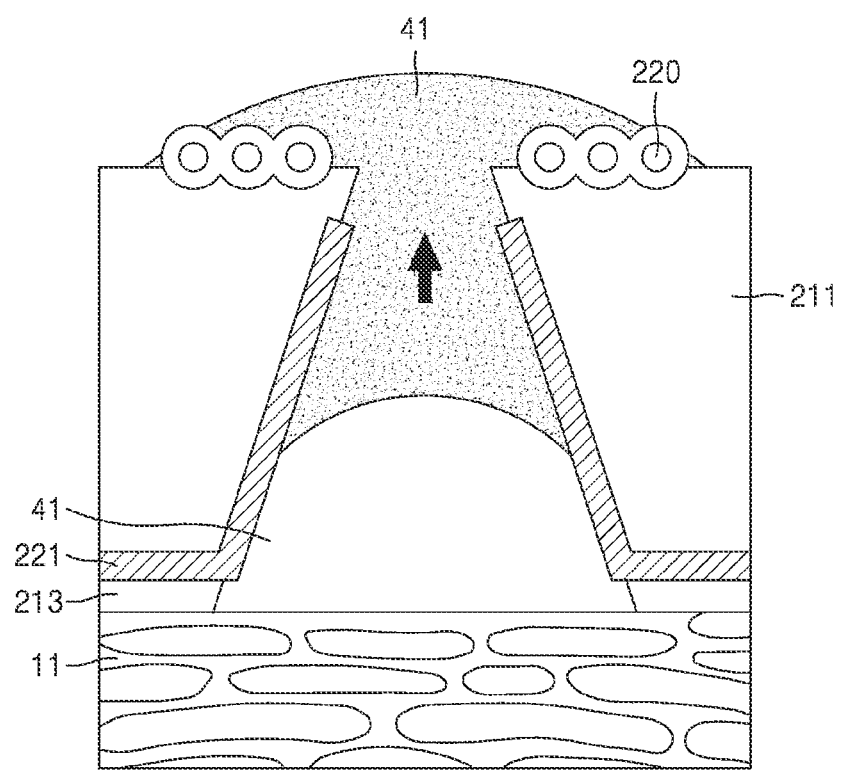

Referring to FIG. 4C, when the discharge of body fluids 41 from the skin 11 of the user 1 stops, the body fluids 41 collected in the body fluid passage 30 may be discharged to the outside of the body fluid passage 30.

For example, when the surface of the body fluid passage 30 is hydrophilic, the body fluids 41 collected in the body fluid passage 30 may be discharged to the outside of the body fluid passage 30 owing to the surface tension of the body fluids 41 in the body fluid passage 30 having a perimeter decreasing in a direction away from a skin attachment surface of the sensor patch 10.

Furthermore, in another example, when the volume of the body fluids 41 collected in the body fluid passage 30 is equal to or greater than a certain value, the body fluids 41 may be discharged to the outside of the body fluid passage 30 owing to a surface tension gradient or an osmotic pressure gradient between the inside and the outside of the body fluid passage 30 caused by a surface treatment 220 performed around the body fluid passage 30.

In the present disclosure, for example, the surface treatment 220 performed on the body fluid sensor 21 may be a treatment of forming nanoparticles (NPs) coated with a polymer to produce an osmotic pressure gradient by a concentration difference and also to produce a surface tension gradient by lowering surface energy.

For example, the body fluid sensor 21 is configured to adjust the movement velocity of the body fluids 41 by adjusting the gradient of osmotic pressure and/or the gradient of surface tension using the structure of the body fluid passage 30 and the degree of doping with the polymer-coated nanoparticles (NPs).

Figure 4D:
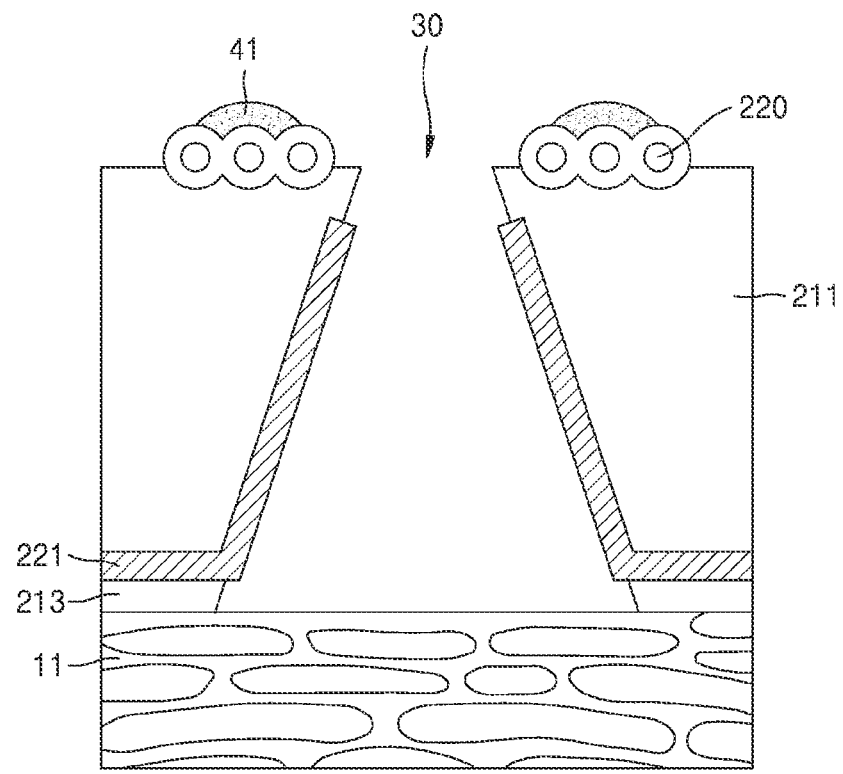

Referring to FIG. 4D, the body fluids 41 discharged to the outside of the body fluid passage 30 may be removed from the body fluid sensor 21 by evaporation. As the body fluids 41 evaporate, the connection between the electrodes 221 of the body fluid sensor 21 through the body fluids 41 may be broken.

Referring to FIGS. 4A to 4D, the body fluid sensor 21 may completely discharge the body fluids 41 secreted from the skin 11 of the user 1 through the body fluid passage 30 without any mechanical driving, and may analyze the discharge of the body fluids 41 for a sufficient period of time based on current flowing through the electrodes 221.

The body fluid sensor 21 is configured to have a sufficient time for analyzing the body fluids 41 by adjusting the movement velocity of the body fluids 41 and may completely discharge the body fluids 41 after analysis.

Figure 5A:
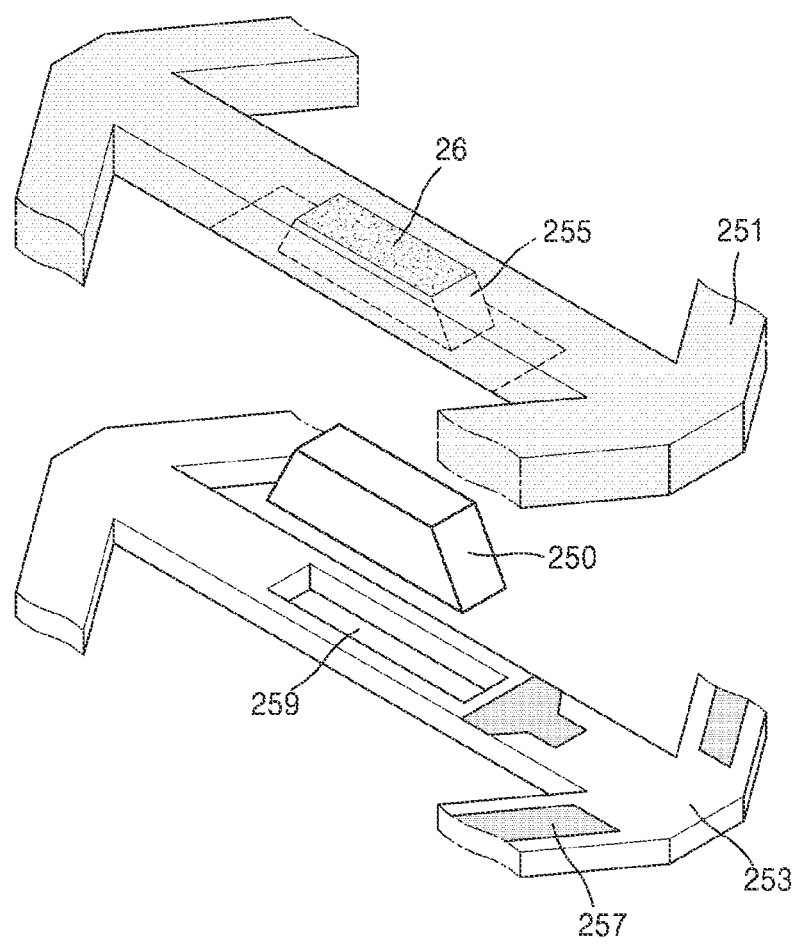
FIGS. 5A to 5C are views illustrating a structure of a bioelectrical sensor according to some embodiments.
Figure 5B:
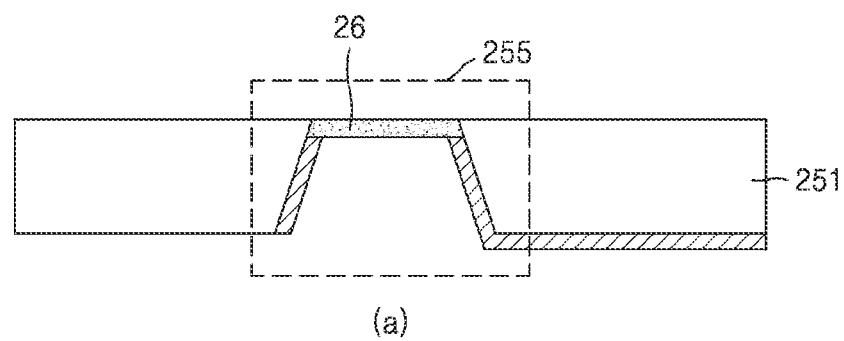
Figure 5B:
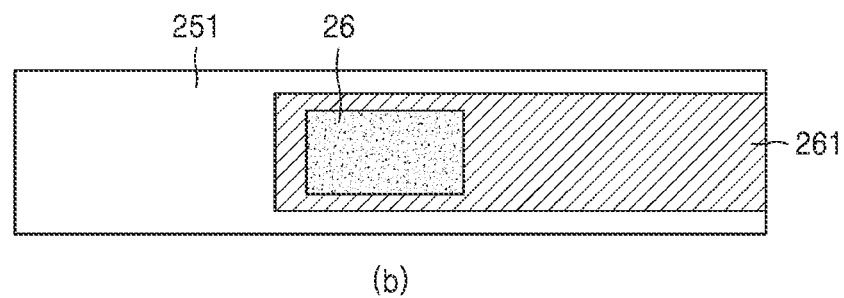
Figure 5C:
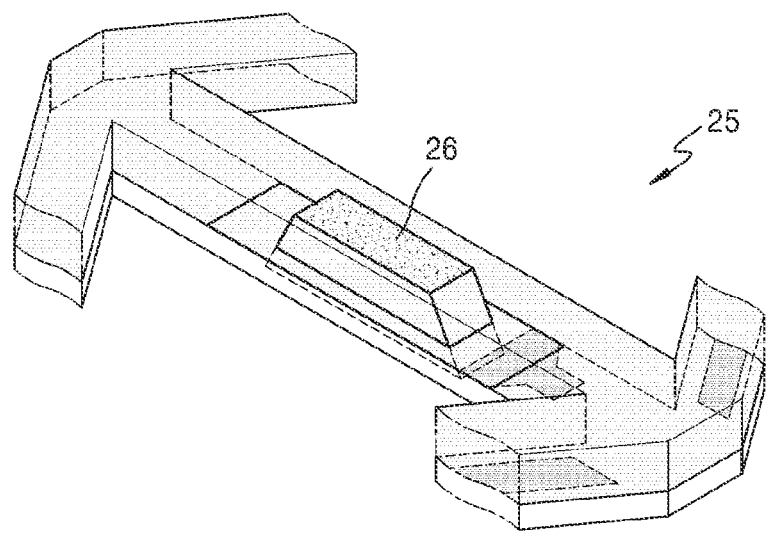

FIGS. 5A to 5C are views illustrating a structure of the bioelectrical sensor 25 according to some embodiments.

In some embodiments, the bioelectrical sensor 25 may include a hydrogel 250 having a lower portion making contact with the skin of the user 1 for absorbing moisture generated from the skin, electrodes 261 configured to detect a current flowing through the hydrogel 250 or biopotential, and an elastic membrane 26 making contact with an upper portion of the hydrogel 250.

Referring to FIGS. 5A and 5B, the bioelectrical sensor 25 may be formed by combining a structural body 251 and a lower plate 253.

Referring to a portion (a) in FIG. 5B, a cross-section of the structural body 251 viewed from a lateral side is illustrated. The structural body 251 may include, for example, a structural body portion 255 configured to fix the hydrogel 250, and the electrodes 261 for sensing a current flowing through the hydrogel 250 or biopotential may be provided on an inner side of the structural body portion 255. The structural body portion 255 may include the elastic membrane 26 which is in contact with an upper portion of the hydrogel 250 fixed by the structural body portion 255.

Referring to a portion (b) in FIG. 5B, a plan view of the structural body 251 viewed from the top is shown. The electrodes 261 provided on the inner side of the structural body portion 255 may surround the hydrogel 250.

For example, the lower plate 253 may include: a third opening 259 for fixing the hydrogel 250; and interconnection electrodes 257 electrically connected to the electrodes 261 for sensing a current flowing through the hydrogel 250 or biopotential. Interconnection electrodes 257 may be formed on the bottom side of the structural body 251.

A lower portion of the hydrogel 250 fixed by the structural body portion 255 and the third opening 259 of the lower plate 253 may be in contact with the skin of the user 1 to absorb moisture generated from the skin.

An upper portion of the hydrogel 250 may be in contact with the elastic membrane 26. The elastic membrane 26 may include at least one opening. The perimeter of each opening of the elastic membrane 26 may increase as the volume of the hydrogel 250 increases and may thus function as a passage through which moisture absorbed in the hydrogel 250 is discharged.

Referring to FIGS. 5A to 5C, the structural body portion 255 and the third opening 259 may be connected to each other by combining the structural body 251 and the lower plate 253 together. The structural body portion 255 and the third opening 259 that are connected to each other may surround and fix the hydrogel 250.

When the sensor patch 10 is attached to the body of the user 1 and thus the bioelectrical sensor 25 included in the sensor patch 10 is brought into contact with the body of the user 1, body fluids discharged from the skin of the user 1 may be absorbed in the hydrogel 250. The body fluids absorbed in the hydrogel 250 may be discharged through the elastic membrane 26 provided on the upper portion of the hydrogel 250.

Figures 6A, 6B:
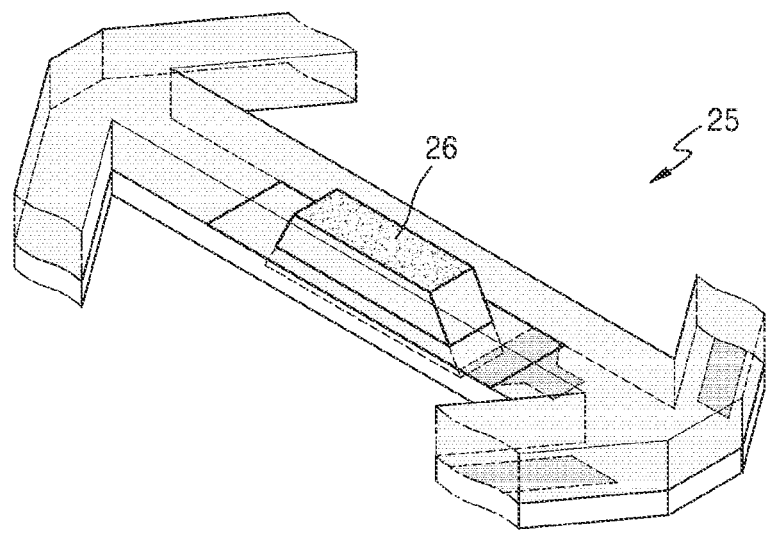
FIGS. 6A and 6B are views illustrating a structure of an elastic membrane according to some embodiments.

FIGS. 6A and 6B are views illustrating a structure of the elastic membrane 26 according to some embodiments.

In some embodiments, the elastic membrane 26 of the bioelectrical sensor 25 may include at least one opening.

Referring to FIG. 6A, in some embodiments, the elastic membrane 26 of the bioelectrical sensor 25 may include a plurality of openings. The plurality of openings included in the elastic membrane 26 may have a fractal structure. For example, the elastic membrane 26 may be cut in a fractal structure to form a plurality of openings.

Cut portions of the elastic membrane 26 may form openings functioning as passages through which body fluids absorbed in the hydrogel 250 are discharged.

Referring to a comparison table in FIG. 6B, when the amount of body fluids of the user 1 which are absorbed in the hydrogel 250 is less than a certain value, that is, the hydrogel 250 is in a less-hydrated state, the openings of the elastic membrane 26 may be in a closed state. When the openings of the elastic membrane 26 are in a closed state, the hydrogel 250 may accumulate body fluids discharged from the skin of the user 1.

However, when the amount of body fluids of the user 1 that are absorbed in the hydrogel 250 is equal to or greater than the certain value, that is, the hydrogel 250 is in a more-hydrated state, the openings of the elastic membrane 26 may be opened. When the openings of the elastic membrane 26 are opened, the body fluids absorbed in the hydrogel 250 may be discharged through the opened openings.

The bioelectrical sensor 25 of the present disclosure may guarantee air permeability by reacting with the moisture of the skin of the user 1 by using the elastic membrane 26 having at least one opening and may properly maintain the water content of the hydrogel 250 by easily controlling the less-hydrated/more-hydrated state of the hydrogel 250.

When the secretion of body fluids of the user 1 varies according to user's surroundings, the bioelectrical sensor 25 may monitor a bioelectrical signal for a relatively long period of time by stably bringing the hydrogel 250, which is hydrated to a proper degree, into contact with the skin of the user 1.

FIGS. 7A to 7D are views illustrating a process of discharging body fluids through the bioelectrical sensor 25 according to some embodiments.

Figure 7A:
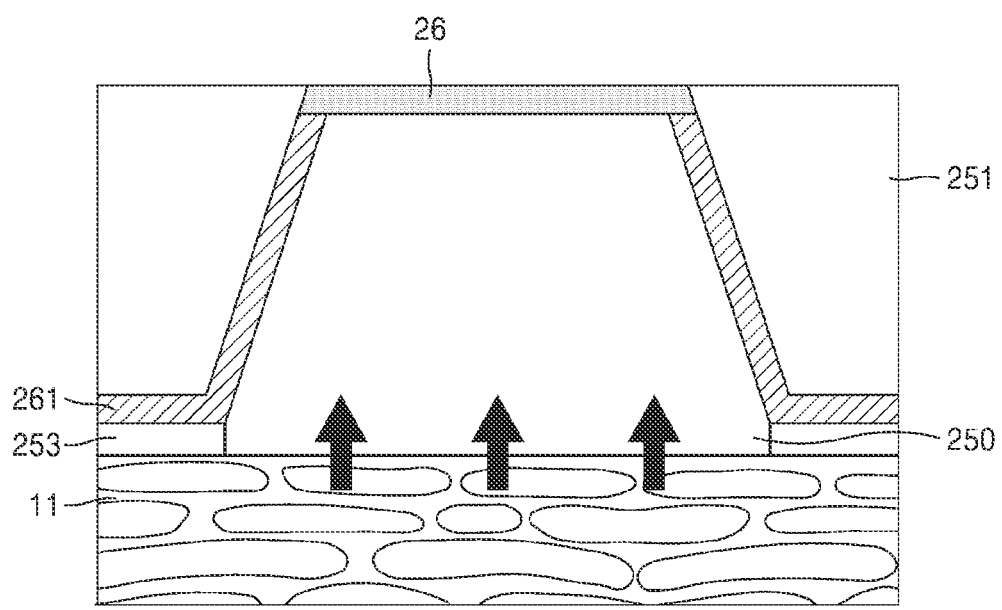
FIGS. 7A to 7D are views illustrating a process of discharging body fluids through the bioelectrical sensor according to some embodiments.

Referring to FIG. 7A, in some embodiments, the lower plate 253 of the bioelectrical sensor 25 may be attached to the skin 11 of the user 1.

The electrodes 261 for sensing a current flowing through the hydrogel 250 or biopotential may be connected to the interconnection electrodes 257. The bioelectrical sensor 25 may generate sensing data relating to an electrophysiological signal based on the sensed current flowing between both electrodes 261 through the hydrogel 250 or sensed biopotential.

The lower portion of the hydrogel 250 may be in contact with the skin 11 of the user 1 and may continuously absorb moisture from the skin 11 of the user 1.

In a state in which the hydrogel 250 absorbs body fluids of the user 1 in an amount less than a predetermined value, that is, when the hydrogel 250 is in a less-hydrated state, the openings of the elastic membrane 26 provided on the upper portion of the hydrogel 250 may be closed. When the openings of the elastic membrane 26 are closed, the hydrogel 250 may accumulate body fluids discharged from the skin 11 of the user 1.

Figure 7B:
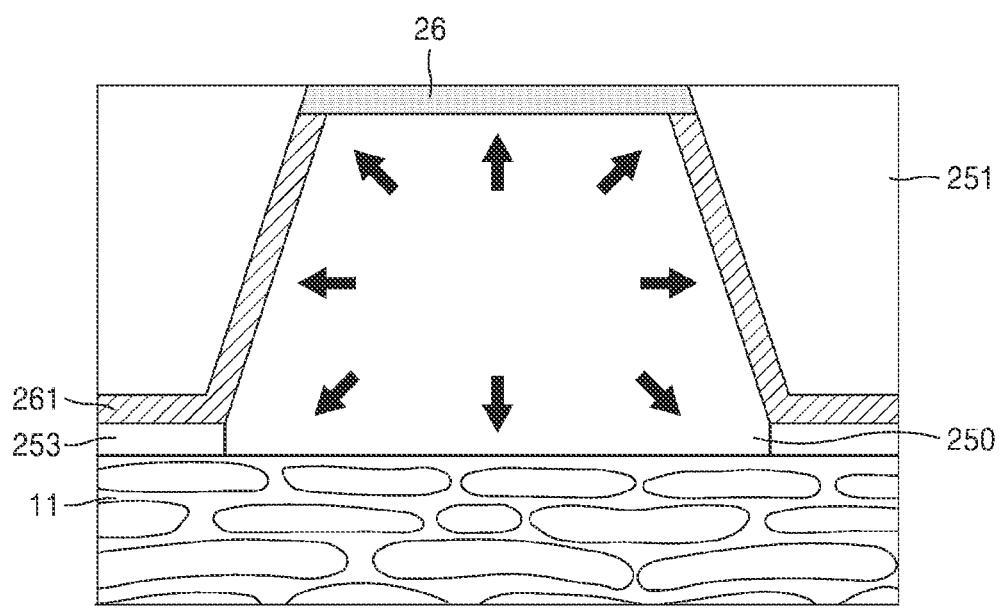

Referring to FIG. 7B, as the body fluids discharged from the skin 11 of the user 1 is absorbed in the hydrogel 250, the volume of the hydrogel 250 may increase. Due to the increase in the volume of the hydrogel 250, pushing force may be applied to the elastic membrane 26 on the upper portion of the hydrogel 250 in a direction away from the skin 11 of the user 1.

Figure 7C:
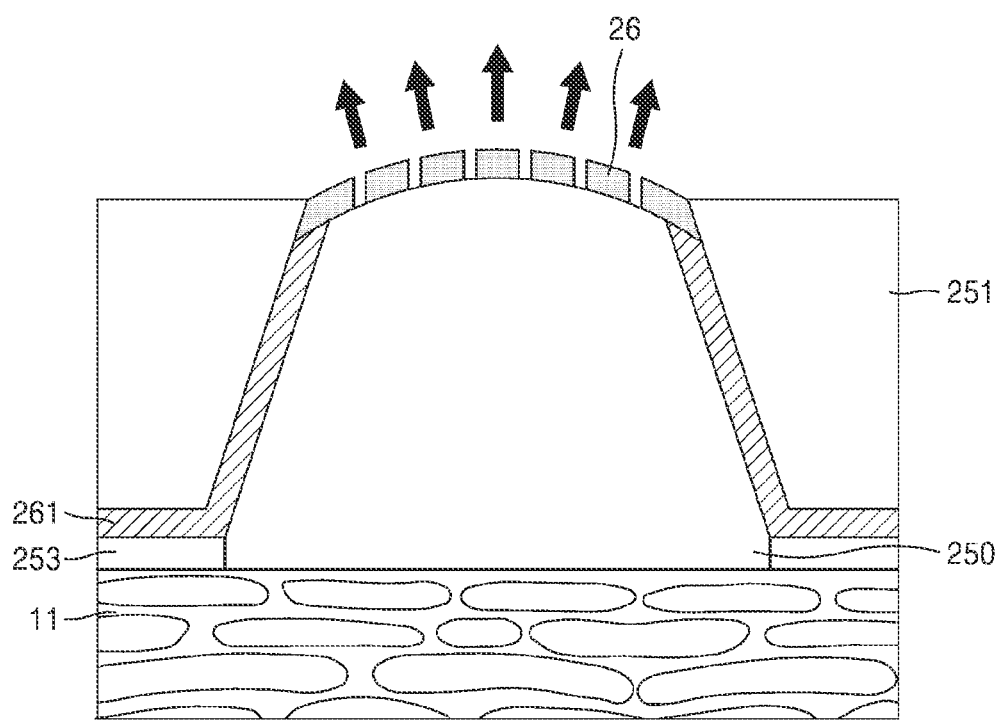

Referring to FIG. 7C, in a state in which the hydrogel 250 absorbs body fluids of the user 1 in an amount equal to or greater than the predetermined value, that is, when the hydrogel 250 is in a more-hydrated state, the openings of the elastic membrane 26 may be opened. The openings of the elastic membrane 26 may be opened by a pushing force applied to the elastic membrane 26 from the hydrogel 250.

When the surface of the hydrogel 250 is exposed through the opened openings of the elastic membrane 26, the body fluids absorbed in the hydrogel 250 may evaporate and may be discharged through the exposed surface of the hydrogel 250.

Figure 7D:
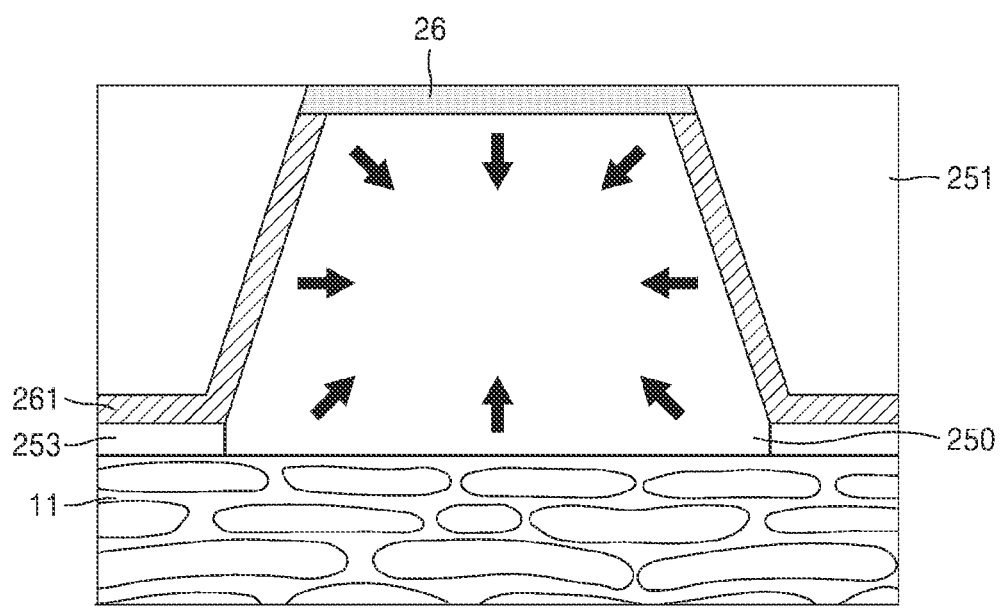

Referring to FIG. 7D, as the body fluids absorbed in the hydrogel 250 are discharged through the openings of the elastic membrane 26, the volume of the hydrogel 250 may decrease. Due to the decrease in the volume of the hydrogel 250, the pushing force applied to the elastic membrane 26 provided on the upper portion of the hydrogel 250 may decrease.

As the pushing force applied to the elastic membrane 26 provided on the upper portion of the hydrogel 250 decreases, the perimeters of the opened openings of the elastic membrane 26 may also decrease, and thus the amount of body fluids discharged per unit time from the exposed surface of the hydrogel 250 through the opened openings of the elastic membrane 26 may accordingly decrease.

As the volume of the hydrogel 250 is reduced by a predetermined value, the openings of the elastic membrane 26 may be eventually closed again.

The bioelectrical sensor 25 of the present disclosure may easily maintain the water content of the hydrogel 250 at a proper level by using the elastic membrane 26 because the perimeter of the at least one opening of the elastic membrane 26 is adjustable according to the water content of the hydrogel.

That is, the bioelectrical sensor 25 of the present disclosure may monitor a bioelectrical signal for a relatively long period of time by stably brining the hydrogel 250, which is properly hydrated, into contact with the skin 11 of the user 1.

Figure 8:
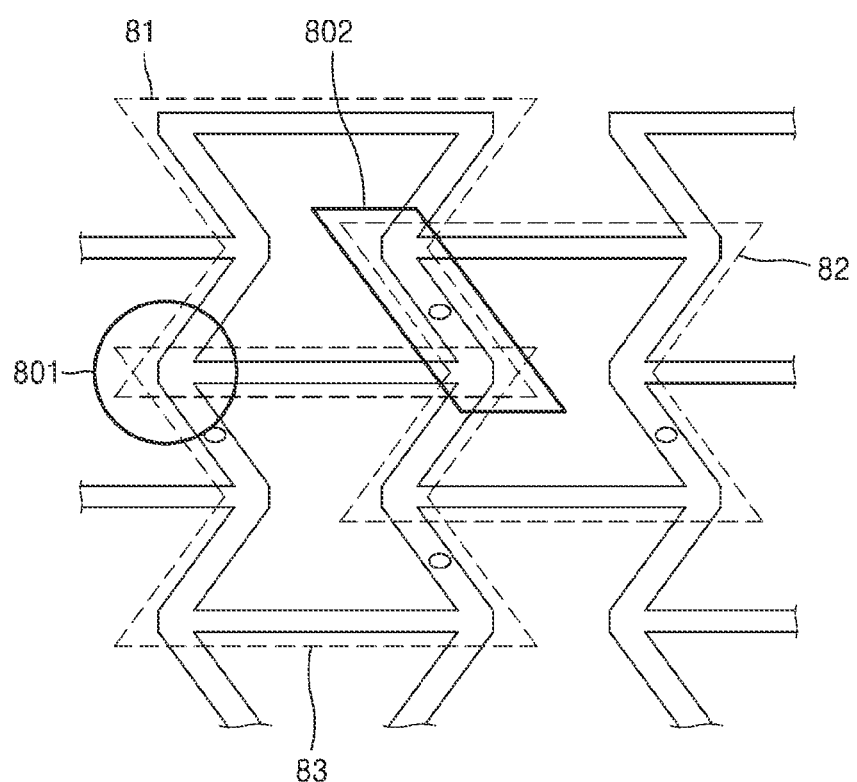
FIG. 8 is a view illustrating a structure of a frame included in the sensor patch according to some embodiments.

FIG. 8 is a view illustrating a structure of the frame 230 of the sensor patch 10 according to some embodiments.

Referring to FIG. 8, in some embodiments, the frame 203 of the sensor patch 10 may include a unit frame 81 of which both lateral middle portions are bent inward toward an opening. In the frame 203, a plurality of unit frames 81 may be repeatedly arranged by a predetermined arrangement method.

For example, in the frame 203, a pair of vertices of a first unit frame 81 may overlap and face a pair of vertices of a third unit frame 83 (refer to an overlapping portion indicated with reference numeral 801).

In another example, the frame 203 may be configured such that a lower end portion on a side of the first unit frame 81 may overlap an upper end portion on another side of a second unit frame 82 (refer to an overlapping portion indicated with reference numeral 802).

In another example, the frame 203 may be configured such that a pair of vertices of the first unit frame 81 may overlap and face a pair of vertices of the third unit frame 83 (refer to the overlapping portion indicated with reference numeral 801), and a lower end portion on an side of the first unit frame 81 may overlap an upper end portion on another side of the second unit frame 82 (refer to the overlapping portion indicated with reference numeral 802). Here, the first unit frame 81, the second unit frame 82, and the third unit frame 83 may form an auxetic structure.

The auxetic structure of the frame 203 of the present disclosure refers to a structure having a negative Poisson's ratio which is the ratio of transverse strain and longitudinal strain when a material is stretched in a specific direction by tension.

The transversal strain and longitudinal strain of normal materials have different signs, and the Poisson's ratio of normal materials have a positive sign. However, the transversal strain and longitudinal strain of the frame 203 of the present disclosure having an auxetic structure may have the same sign, and the Poisson' ratio of the frame 203 may have a negative sign. That is, when the frame 203 is subjected to longitudinal stress, the longitudinal length of the frame 203 may increase, and the transversal length of the frame 203 may also increase.

In addition, among various mechanical metastructures which the frame 203 of the present disclosure may have, an open-type auxetic structure is a stable design pattern that may be brought into contact with the surface of the skin having a random curvature resulting in strain-free regions inside the frame 203 although the frame 203 is subjected to various deformations. That is, the frame 203 of the present disclosure may be attached to various curved surfaces without being wrinkled or folded, and may thus have high adhesion to the skin of a user.

Figure 9A:
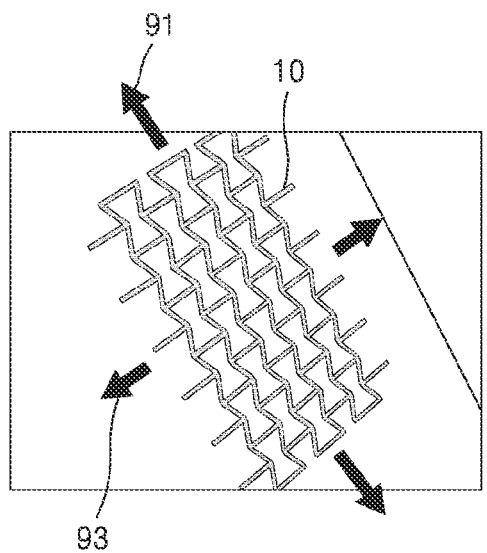
FIGS. 9A and 9B are views illustrating a sensor patch having an auxetic structure according to some embodiments.
Figure 9B:
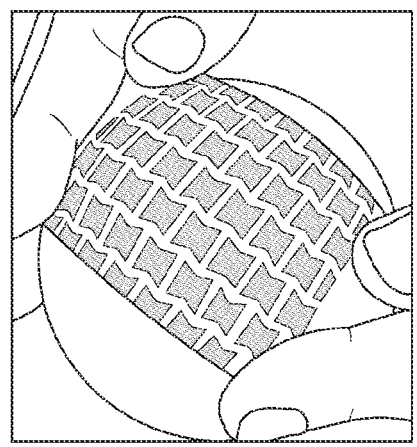

FIGS. 9A and 9B are views illustrating a sensor patch 10 having an auxetic structure according to some embodiments.

Referring to FIG. 9A, in some embodiments, a frame of the sensor patch 10 may include a plurality of unit frames combined in an auxetic structure. When the sensor patch 10 is subjected to tensile stress in a first direction 91 parallel to the surface of the skin to which the sensor patch 10 is attached, the length of the frame may increase in the first direction 91 and also in a second direction 93 which is parallel to the surface of the skin and is perpendicular to the first direction 91.

Thus, the frame of the sensor patch 10 having an auxetic structure may have relatively high adhesion to the skin of a user which may be variously deformed according to various conditions such as skeletal characteristics, muscle characteristics, body movements, and external forces.

FIG. 9B illustrates an example in which the sensor patch 10 including the frame having an auxetic structure is attached to a curved surface according to some embodiments.

That is, the sensor patch 10 of the present disclosure may have high adhesion to the skin of a user having a curved shape owing to the frame having an auxetic structure. In addition, the sensor patch 10 of the present disclosure allows the skin of a user which has a curvature to be exposed through at least one opening surrounded by the frame, thereby guaranteeing moisture permeability and air permeability.

In the present disclosure, the term "sensor" may be a hardware component such as a processor or a circuit, and/or a software component executable by a hardware component such as a processor.

The description of the present disclosure is for illustrative purposes only, and it will be understood by those of ordinary skill in the art that modifications and changes in form may be easily made without departing from the technical ideas and essential features of the present disclosure. Therefore, the above-described embodiments should be considered in a descriptive sense only and not for purposes of limitation. For example, each element described above as an individual element may be provided in a distributed manner, and elements described above as being distributed may be provided in a combined form.

According to the present disclosure, at least one sensor for measuring a biosignal is provided on the frame surrounding at least one opening, and thus it may be possible to continuously obtain a biosignal of a user for a long period of time while guaranteeing air permeability and moisture permeability.

It should be understood that embodiments described herein should be considered in a descriptive sense only and not for purposes of limitation. Descriptions of features or aspects within each embodiment should typically be considered as available for other similar features or aspects in other embodiments. While one or more embodiments have been described with reference to the figures, it will be understood by those of ordinary skill in the art that various changes in form and details may be made therein without departing from the spirit and scope of the disclosure as defined by the following claims.

What is claimed is:

1. A sensor patch configured to be attached to skin of a user, the sensor patch comprising:
at least one uncovered opening; and
a frame surrounding the at least one uncovered opening, wherein the frame comprises a plurality of connected unit frames that are repeatedly arranged, each of the connected unit frames including at least one sensor configured to measure a biosignal of the user, and
wherein
the at least one sensor comprises at least one of:
a body fluid sensor configured to detect a body fluid of the user;
a bioelectrical sensor configured to detect an electrophysiological signal of the user; and
a pulse sensor configured to detect a pulse of the user, and
the body fluid sensor comprises:
at least one body fluid passage configured to discharge the body fluid in a direction away from the skin of the user; and
an electrode configured to detect a current flowing through the body fluid of the user which is discharged through the body fluid passage.

2. The sensor patch of claim 1, wherein the body fluid passage has a perimeter unchanging, decreasing or increasing in a direction away from a skin attachment surface of the sensor patch.

3. The sensor patch of claim 1, wherein the bioelectrical sensor comprises:
a hydrogel that has a lower portion making contact with the skin of the user and absorbs moisture from the skin of the user;
an electrode configured to detect a current flowing through the hydrogel or biopotential; and
an elastic membrane making contact with an upper portion of the hydrogel.

4. The sensor patch of claim 3, wherein
the elastic membrane comprises
at least one opening, and
as the hydrogel increases in volume, the at least one opening increases in perimeter such that the moisture absorbed in the hydrogel is discharged through the at least one opening.

5. The sensor patch of claim 1, wherein the frame comprises at least one electrode array connected to the at least one sensor.

6. The sensor patch of claim 1, wherein each unit frame comprises lateral middle portions that are bent inward toward the at least one uncovered opening.

7. The sensor patch of claim 6, wherein the frame comprises:
a first unit frame; and
a second unit frame,
wherein a lower end portion on a side of the first frame is an upper end portion on another side of the second unit frame.

8. The sensor patch of claim 1, wherein the plurality of unit frames are repeatedly arranged such that a pair of vertices of a unit frame overlaps and faces a pair of vertices of another unit frame.

9. The sensor patch of claim 1, wherein when the frame is subjected to tensile stress in a first direction parallel to a surface of the skin to which the sensor patch is attached, the frame increases in length in the first direction and accordingly in a second direction which is parallel to the surface of the skin and perpendicular to the first direction.

* * * * *